US00PP18331P2

(12) United States Plant Patent
Meadows, Jr. et al.

(10) Patent No.: US PP18,331 P2
(45) Date of Patent: Dec. 18, 2007

(54) ***LOROPETALUM CHINENSIS* VARIETY *RUBRUM* PLANT NAMED 'SHANG-HI'**

(50) Latin Name: *Loropetalum chinensis*
Varietal Denomination: Shang-hi

(75) Inventors: Thomas Dennis Meadows, Jr., Silverhill, AL (US); James Bryan Berry, Grand Saline, TX (US)

(73) Assignee: Plant Development Services, Inc., Loxley, AL (US)

( * ) Notice: Subject to any disclaimer, the term of this patent is extended or adjusted under 35 U.S.C. 154(b) by 0 days.

(21) Appl. No.: 11/488,651

(22) Filed: Jul. 19, 2006
(Under 37 CFR 1.47)

(51) Int. Cl.
*A01H 5/00* (2006.01)

(52) U.S. Cl. ..... Plt./226
(58) Field of Classification Search ..... Plt./226
See application file for complete search history.

*Primary Examiner*—Kent Bell
*Assistant Examiner*—Annette H Para
(74) *Attorney, Agent, or Firm*—Breiner & Breiner, LLC

(57) ABSTRACT

A new and distinct variety of *Loropetalum chinensis* variety *rubrum* plant named 'Shang-hi', characterized by its dense, upright, globose growth habit, persistent dark purple foliage color, and abundance of dark pink flowers.

1 Drawing Sheet

Genus Species Variety: *Loropetalum chinensis* Variety *rubrum.*
Varietal Denomination: 'Shang-hi'.

BACKGROUND OF THE INVENTION

The present invention relates to a new and distinct variety of the genus *Loropetalum* and a member of the Hammaelidaceae family. This new *Loropetalum* variety, hereinafter referred to as 'Shang-hi' was discovered by Thomas Dennis Meadows, Jr. and James Bryan Berry in March, 2003. 'Shang-hi' was found as an openly pollinated seedling of *Loropetalum chinensis* variety *rubum* (unpatented), maintained by Plant Development Services Inc., in Loxley, Ala. The values of this new cultivar lies in its dense, upright, globose growth habit, persistent dark purple foliage color, and abundance of dark pink flowers. 'Shang-hi' has retained many of the outstanding attributes of its parent variety, in particular its tolerance of heat and disease, which makes it adaptable to culture in most of the Sunbelt States. As with the parent variety, the plant of this invention may be advantageously employed as a specimen appointment, in either formal or informal groupings, and is quite attractive in mass plantings. 'Shang-hi' serves well in foundation plantings and is adaptable for culture as a potted plant. 'Shang-hi' is responsive to pruning and training and may be employed in forming dense, attractive hedges, and maintained without an excessive amount of care. This plant is easy to care for and maintain in size due to its short internodes, heavy branching, and dense canopy. Its natural propensity to remain small to maturity makes it valuable for landscape uses in smaller home gardens which require plants that do not outgrow their intended mature dimensions.

Asexual propagation of the new plant by cuttings has been under Mr. Meadows' direction in Loxley, Ala. The new plant retains its distinctive characteristics and reproduces true to type in successive generations of asexual reproduction. The plant cannot be reproduced true from seed.

SUMMARY OF THE INVENTION

The following are the most outstanding and distinguishing characteristics of this new cultivar when grown under normal horticultural practices in Loxley, Ala.

1. Dense, upright and globose in nature.
2. The upper surface of the mature leaf is a lustrous dark purple color throughout the year.
3. Underside of leaf is an attractive grayish purple color.
4. Fast growth rate under normal fertilization and moisture conditions.
5. Hardy to Zone 7.
6. Tolerates full sun to part shade.
7. Heat tolerant.
8. Easily porpagated with semi-hardwood cuttings in late spring through the summer.
9. Requires little pruning but is tolerant if pruning is needed.
10. Relatively pest resistant.
11. Good specimen plant.
12. Good foundation plant.
13. Makes a very good hedge or screen.
14. Very desirable in planters.
15. The flowers are dark pink and profuse.

DESCRIPTION OF THE DRAWINGS

This new *Loropetalum chinensis* variety *rubrum* cultivar is illustrated by the accompanying photographic prints in which:

FIG. 1 is a photograph of a close-up showing the flower, buds, foliage and stem color, as well as flower size and form.

FIG. 2 is a photograph showing the dense, upright, and globose growth habit of a three gallon plant.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of *Loropetalum* based on observations made of two year old plants grown in three gallon containers in commercial production practices, in greenhouses, and in established landscape plantings in Loxley, Ala. and including a comparison with *Loropetalum chinensis* variety *rubrum, Loropetalum chinensis* 'Bill Wallace' U.S. Plant Pat. No. 15,277, and *Loropetalum chinensis* 'Hindwarf' U.S. Plant Pat. No. 12,203.

Distinctive Characteristics:

TABLE 1

| Characteristic | *Loropetalum c.* var. *rubrum* 'Shang-hi' | *Loropetalum c.* Var. *rubrum* | *Loropetalum c.* 'Bill Wallace' PP#15277 | *Loropetalum c.* 'Hindwarf' PP#12203 |
|---|---|---|---|---|
| Height (Mature) | 4-5 feet | 10-12 feet | 9 inches | 2 feet |
| Width (Mature) | 3-4 feet | 8-9 feet | 25 inches | 3-6 feet |
| Leaf Length | ⅞-1⅜ inches | 1½-2¼ inches | 1⅛ inches | 7/16-1 inch |
| Leaf Width | ⅝-⅞ inch | ¾-1⅛ inches | ⅝ inch | ⅜-⅝ inch |
| Growth Habit | Dense, upright, Globose | Upright, Spreading | Outwardly Spreading, Procumbent | Compact prostrate to mounding |
| Foliage Color (Immature) | Greyed-Purple G. 187B | Yellow-Green G. 147A overlain with Greyed-Purple G. 187B | Yellow-Green G. 147A overlain with Greyed-Purple G. 187A | Near Greyed-Purple G 183A, 53A and 187A |
| Foliage Color (Mature) | Greyed-Purple G. 187A | Greyed-Purple G. 187A to Green G. 139A | Greyed-Green G. 189A underlain with 187A | Near Yellow-Green G. 147A and 187A |
| Flower Color | Red-Purple G. 61B | Red-Purple G. 67B | None observed | Red G. 55B to 51A, 53C, 52A and 53D |
| Leaf Shape | Elliptical | Ovate | Elliptical | Ovate |

The female, or seed parent, of 'Shang-hi' is *Loropetalum chinensis* variety *rubrum* (unpatented) which is a native of China, and was first discovered in 1928 in Hunan Province. It was introduced to the United States in the 1980's.

*Loropetalum chinensis* variety *rubrum, Loropetalum chinensis* 'Bill Wallace' U.S. Plant Pat. No. 15,277, and *Loropetalum chinensis* 'Hindwarf' U.S. Plant Pat. No. 12,203 are well known in the industry and are comparable to 'Shang-hi' in that all have reddish purple foliage color at some point during the year. However, there are many differences. The dark foliage of 'Shang-hi' is persistent throughout the year whereas the foliage of each of the comparable varieties is green at some point during the year. The growth habit of 'Shang-hi' is dense, upright and globose to 5 feet tall compared to the parent variety which is a much taller grower with the a spreading habit. The cultivars 'Bill Wallace' and 'Hindwarf' are both more prostrate in habit.

Classification

Botanical: *Loropetalum chinensis* variety *rubrum* 'Shang-hi'.

Parentage: Openly pollinated seedling of *Loropetalum chinensis* variety *rubrum.*

Commercial: Broadleaf evergreen.

Form: Dense, upright and globose.

Height: 4–5 feet.

Width: 3–4 feet.

Growth Rate: Fast under normal fertilization and moisture conditions. Semi-hardwood cuttings taken in late spring and through the summer produce rooted cuttings in four to five months in Loxley, Ala. Root development is vigorous and finely branched. In a period of four years from a rooted cutting, the plant reaches a height of 3 feet and a spread of 2 feet under normal growing conditions in Loxley, Ala. The plant normally grows at the rate of about 9 inches or more per year and reaches a height of 5 feet and a spread of 4 feet at maturity while maintaining a dense habit due to the abundant branch development.

Foliage: Alternate, simple, evergreen, elliptic, sparsely stellate-pubescent, coriaceous, almost flat, and varying in size from ⅞ inch to 1⅜ inches long and ⅝ inch to ⅞ inch wide. The petioles are ⅛ inch to 3/16 inch long, 1/32 inch in diameter, heavily stellate-pubescent and Greyed-Purple Group 187B. The venation pattern is pinnate. The base of the leaf is oblique, the margin entire, and the apex acute. The upper surface of the immature leaf is Greyed-Purple Group 187B and the underside is Purple Group 97D underlain with Greyed-Purple Group 187B. Immature midribs and veins are depressed on the upper side (Greyed-Purple Group 187B) and prominent on the underside (Purple Group 79D). These immature leaf colors last three to four weeks in Loxley, Ala. The upper surface of the mature leaf is closest to but darker than Greyed-Purple Group 187A with closest to but darker than Yellow-Green Group 147A undertones. Mature midribs and veins are depressed on the upper side (Greyed-Purple Group 187A) and prominent on the under side (Greyed-Green Group 194C). These mature leaf colors are persistent throughout the winter. The paired foliaceous stipules are ⅛ inch to 3/16 inch long and 1/32 inch to 1/16 inch wide. The upper surface and under surface are Greyed-Purple Group 187A. The stipules are caducous.

In 2005, the date of initial spring growth was March 10, in Loxley, Ala. After the initial spring flush there was almost continuous slow growth until fall, ending October 28, also in Loxley, Ala. When grown in full sun, the internode length of this plant is ¼ inch to ⅝ inch. When grown in light shade the internode length is ⅜ inch to ⅞ inch. As would be expected, a plant grown in the shade results in a taller, less dense plant with larger leaves.

Stems: The young stems are Greyed-Purple Group 187A and heavily stellate-pubescent. During the second growing season they become Brown Group 200C. The pitch is solid and uniform. Young and older stems are densely branched.

Flowers: Perfect, Red-Purple Group 61A (upper surface and under surface), glabrous, four strap-shaped petals. The flowers form a loose funnel, are borne on current season's growth, and are non-fragrant; they last on the plant in the garden five to seven days. Tight buds at 3/16 inch are orbicular, Red-Purple Group 63B and pubescent. Six to eight flowers form globose heads on branchlet terminals and occasionally one to two flowers in the leaf axils. Flowering occurs from early March to late March with light repeat blooming throughout the growing season. These racemes are 1¼ inches to 1½ inches in diameter by ⅝ inch to ⅞ inch in depth and abundantly cover the plant. The flowers are attached in a circular pattern to short peduncles which are pubescent, 1/16 inch long, 1/32 inch in diameter and Red-Purple Group 63B. The four petals which arise from the calyx tube at the sepal base are linear, crinkled, ⅝ inch to ⅞ inch long, 1/16 inch to ⅛ inch wide, with retuse apexes and entire margins. There are four stamens 1/32 inch long, Red-Purple Group 63A, with anthers also Red-Purple Group 63A. Pollen matures to Yellow-Green Group 11D and is produced in very small amounts. The two pistils are 1/32 inch long and Red-Purple Group 63A. The ovary is inferior and two-celled. Each flower has four sepals that have entire revolute margins which are 1/16 inch long, 1/16 inch wide, ovate, and fused into a calyx. The calyx is 3/16 inch in diameter, 3/16 inch in depth, pubescent and Red-Purple Group 63B outer and surface and Red-Purple Group 63A inner surface.

Fruit: Woody, scabrous, ovoid, 3/16 inch to 5/16 inch long, 1/8 inch to 1/4 inch in diameter, two-celled capsule, one seed per cell. Mature plants produce 75 to 100 fruits which are Yellow-Green Group 146B. Seeds are 1/8 inch to 3/16 inch long, 1/16 inch to 1/8 inch in diameter, Brown Group 200C, and mature in the fall.

Culture: Grows well in a wide range of conditions and tolerates sun to part shade. Prefers a moist, well-drained soil that is rich in organic matter. Responds well to mulching and medium applications of fertilizer; prefers pH 6 to 7. Very little pruning is needed. Adaptable to containers and above ground planters. Makes a good foundation plant or informal hedge with excellent foliage and flower contrast. Ideal for coastal regions and warmer parts of the Piedmont. Cold hardiness and drought resistance are comparable to the parent variety. Propagated with semi-hardwood cuttings in late spring through the summer.

Disease and Insect Resistance: Resistance to disease and insects common to plants of *Loropetalum* has not been observed.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claim.

It is claimed:

1. A new and distinct variety of *Loropetalum chinensis* variety *rubrum* plant named 'Shang-hi' as illustrated and described.

* * * * *

FIGURE 1
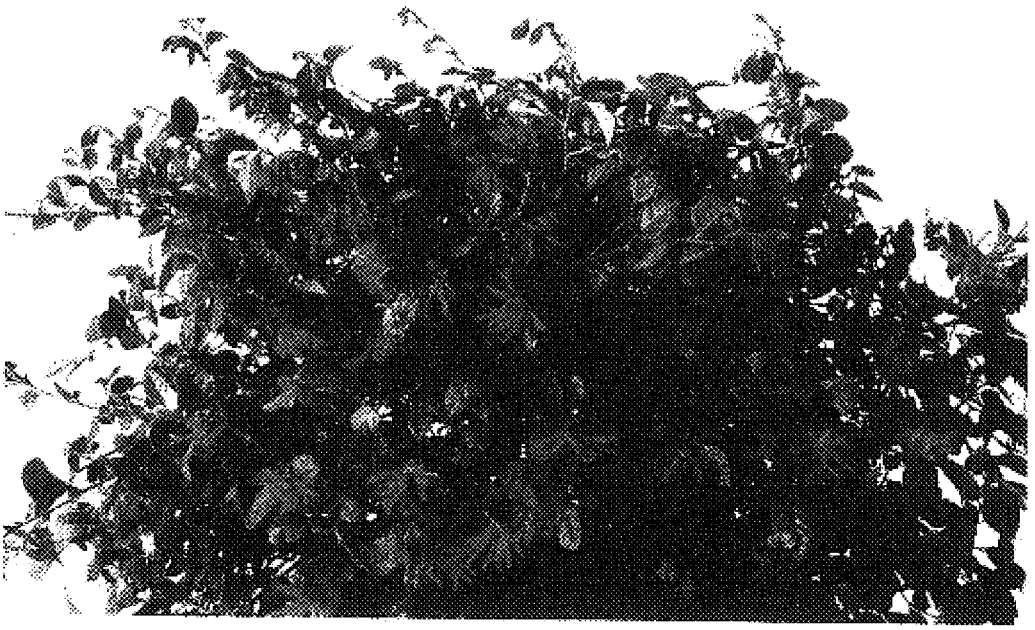
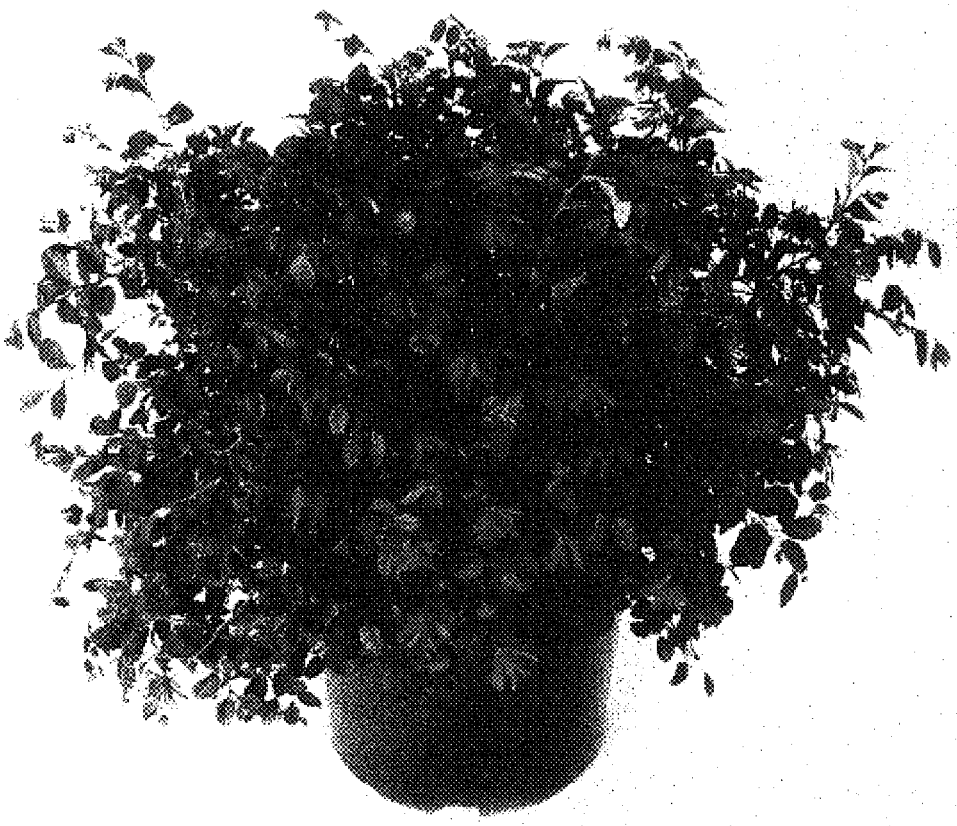
FIGURE 2